United States Patent
Swain et al.

(10) Patent No.: US 9,597,497 B2
(45) Date of Patent: Mar. 21, 2017

(54) WIRELESS FOOTSWITCH AND FUNCTIONAL ELECTRICAL STIMULATION APPARATUS

(71) Applicant: Salisbury NHS Foundation Trust, Salisbury (GB)

(72) Inventors: Ian Douglas Swain, Salisbury (GB); Stacey Michael Finn, Salisbury (GB); Dominic Scott Nolan, Salisbury (GB); Robert Peter Batty, Southampton (GB)

(73) Assignee: Salisbury NHS Foundation Trust, Salisbury (GB)

( * ) Notice: Subject to any disclaimer, the term of this patent is extended or adjusted under 35 U.S.C. 154(b) by 0 days.

(21) Appl. No.: 14/352,569

(22) PCT Filed: Oct. 22, 2012

(86) PCT No.: PCT/GB2012/052612
§ 371 (c)(1),
(2) Date: Apr. 17, 2014

(87) PCT Pub. No.: WO2013/061038
PCT Pub. Date: May 2, 2013

(65) Prior Publication Data
US 2014/0276236 A1    Sep. 18, 2014

(30) Foreign Application Priority Data

Oct. 27, 2011    (GB) .................................. 1118580.8

(51) Int. Cl.
*A61N 1/36*    (2006.01)
*A43B 3/00*    (2006.01)
(Continued)

(52) U.S. Cl.
CPC ........ *A61N 1/36003* (2013.01); *A43B 3/0005* (2013.01); *A43B 3/0031* (2013.01);
(Continued)

(58) Field of Classification Search
CPC ............ A61N 1/36003; A61N 1/36014; A61N 1/0484; A61N 2005/0645; A61N 5/0613;
(Continued)

(56) References Cited

U.S. PATENT DOCUMENTS

| 6,507,757 | B1 | 1/2003 | Swain |
| 7,632,239 | B2 | 12/2009 | Dar et al. |

(Continued)

FOREIGN PATENT DOCUMENTS

| GB | 2368019 A | 4/2002 |
| KR | 2012-0007675 A | 1/2012 |

(Continued)

OTHER PUBLICATIONS

"Great Britain Application Serial No. GB1118580.8, Search Report mailed Jan. 16, 2013", 5 pgs.
(Continued)

*Primary Examiner* — Deborah Malamud
(74) *Attorney, Agent, or Firm* — Schwegman Lundberg & Woessner, P.A.

(57) ABSTRACT

A shoe insole has a cavity configured to provide an internal pocket open to a face of said insole, conveniently the lower face, the cavity having a length greater than its width and being directed generally along the length of the insole. A segmented structure is slideably insertable into said cavity within it is removably retained, the segments being disposed along the cavity and housing a pressure sensor, sensor state monitoring circuits, a wireless transceiver and a battery, adjacent segments being electrically connected together and hinged together by pairs of laterally spaced connector bars each mechanically connected together by links configured to maintaining the spacing between segments while permitting flexion between adjacent segments under loads encountered during walking.

18 Claims, 7 Drawing Sheets

(51) Int. Cl.
*A61B 5/00* (2006.01)
*A61B 5/103* (2006.01)
*A43B 17/00* (2006.01)
*A61N 1/04* (2006.01)
*A61B 5/11* (2006.01)

(52) U.S. Cl.
CPC ............ *A43B 17/00* (2013.01); *A61B 5/0002* (2013.01); *A61B 5/1038* (2013.01); *A61B 5/6807* (2013.01); *A61B 5/6829* (2013.01); *A61B 5/112* (2013.01); *A61B 2562/0219* (2013.01); *A61B 2562/0247* (2013.01); *A61B 2562/164* (2013.01); *A61N 1/0456* (2013.01); *A61N 1/36014* (2013.01)

(58) Field of Classification Search
CPC .. A61N 1/0452; A61N 1/365; A61N 1/36535; A61N 1/36542; A61B 5/1038; A61B 5/6807; A61B 5/6828; A61B 2562/0219; A61B 5/0245; A61B 5/1116; A61B 5/1123; H01H 3/14; A43B 3/0005; A61H 2201/165; A61H 2201/5084; A61H 2205/106; A61H 3/00
See application file for complete search history.

(56) References Cited

U.S. PATENT DOCUMENTS

| | | | |
|---|---|---|---|
| 7,758,523 B2 | 7/2010 | Collings | |
| 2003/0009308 A1 | 1/2003 | Kirtley | |
| 2003/0163287 A1* | 8/2003 | Vock | A43B 3/0005 702/187 |
| 2004/0173220 A1* | 9/2004 | Harry | A43B 3/0005 128/892 |
| 2007/0112285 A1 | 5/2007 | Dar et al. | |
| 2007/0204687 A1 | 9/2007 | Haselhurst | |
| 2008/0306410 A1 | 12/2008 | Kalpaxis et al. | |
| 2009/0043357 A1 | 2/2009 | Tong et al. | |
| 2009/0069865 A1 | 3/2009 | Lasko et al. | |
| 2010/0324455 A1 | 12/2010 | Rangel | |
| 2011/0214501 A1 | 9/2011 | Ross et al. | |

FOREIGN PATENT DOCUMENTS

| | | |
|---|---|---|
| WO | WO-2006/067434 A1 | 6/2006 |
| WO | WO-2009/089406 A2 | 7/2009 |
| WO | WO-2011/042736 A1 | 4/2011 |
| WO | WO-2013/061038 A2 | 5/2013 |

OTHER PUBLICATIONS

"International Application Serial No. PCT/GB2012/052612, Informal Comments filed Mar. 21, 2014", 4 pgs.
"International Application Serial No. PCT/GB2012/052612, International Search Report mailed Jul. 4, 2013", 8 pgs.
"International Application Serial No. PCT/GB2012/052612, Written Opinion mailed Jul. 4, 2013", 13 pgs.
Burridge, J. H, et al., "Functional electrical stimulation: a review of the literature published on common peroneal nerve stimulation for the correction of dropped foot", *Reviews in Clinical Gerontology*, 8, (1998), 155-161.
Liberson, W. T., et al., "Functional electrotherapy in stimulation of the peroneal nerve synchronized with the swing phase of gait of hemiplegic patients", *Arch. Phys. Med. Rehabil.*, 42, (1961), 102-105.
"International Application Serial No. PCT/GB2012/052612, International Preliminary Report on Patentability mailed May 8, 2014", 15 pgs.

* cited by examiner

WIRELESS FOOTSWITCH AND FUNCTIONAL ELECTRICAL STIMULATION APPARATUS

RELATED APPLICATIONS

This application is a U.S. National Stage Application filed under 35 U.S.C. §371 of International Application Serial Number PCT/GB2012/052612, filed Oct. 22, 2012 and published as WO 2013/061038 A3 on May 2, 2013, which claims priority to United Kingdom Patent Application Serial No. 1118580.8, filed Oct. 27, 2011; which applications and publication are incorporated herein by reference in their entirety.

FIELD OF THE INVENTION

The present invention relates to a wireless footswitch module, to a wireless footswitch in which a module as aforesaid fits into an insole, and to a FES system comprising a wireless footswitch and a FES device for attachment to the human body for stimulation of one or more muscle groups in response to signals from said stimulator. It also relates to the use of the stimulator for treating a variety of conditions, in embodiments for treating dropped foot

BACKGROUND TO THE INVENTION

In embodiments, the invention provides apparatus for applying an electrical stimulus to a person's leg in timed relationship to leg movement during walking in order to achieve a benefit.

For example, a person who has a dropped foot is unable to lift his or her toes clear of the ground during the swing phase of walking. Such a problem is seen in people who have either a peripheral nerve lesion, as a result of trauma or disease, or an upper motor neuron lesion. It is the latter that responds to neuromuscular stimulation. Lesions of the lower motor neurons result in destruction of the neural pathway so that muscle contraction can be achieved only through direct stimulation of the muscle fibers. Functional electrical stimulation may therefore be suitable for the treatment of patients following stroke, multiple sclerosis, spinal cord injury T-12 and above, Parkinson's disease, cerebral palsy, head injury and familial or hereditary spastic paraparesis.

The first reference to functional electrical stimulation (FES) is the work by Liberson et al, "Functional electrotherapy in stimulation of the peroneal nerve synchronized with the swing phase of gait of hemiplegic patients", *Arch. Phys. Med. Rehabil.* 42, 202-205 (1961). At this time electrotherapy was commonplace, but functional electrotherapy was a new concept. Liberson defined it as follows: ' . . . to provide the muscles with electrical stimulation so that at the very time of the stimulation the muscle contraction has a functional purpose, either in locomotion or in prehension or in other muscle activity. In other words, functional electrotherapy is a form of replacement therapy in cases where impulses coming from the central nervous system are lacking.'

Liberson used a portable stimulator to correct drop foot during walking A train of pulses of 20-250 μsec duration, frequency 30-100 Hz and maximum peak current 90 mA was applied through conductive rubber electrodes. The negative (active) electrode was placed over the common peroneal nerve below the knee and the large indifferent electrode either on the thigh or on the lower leg. The stimulator was worn in the pocket and a heel switch was used to trigger the stimulus during the swing phase of the gait cycle. The switch was worn within the shoe or on the foot on the affected side so that the electrical circuit was interrupted during the stance phase, when the weight was on the heel, and allowed to flow when the heel was lifted during the swing phase. Liberson was enthusiastic about the results, reporting that all the subjects experienced considerable improvement in gait. Despite improvements in the apparatus used, the basic idea of FES has remained unchanged. Sixteen papers on the topic published in the period 1960-1977 have been reviewed by J. H. Burridge et al, *Reviews in Clinical Gerontology*, 8, 155-161 (1998).

U.S. Pat. No. 6,507,757 (Swain, the contents of which are incorporated herein by reference) is concerned with improving the reliability of the foot switch. In one aspect it discloses a functional electrical stimulator for attachment to a leg comprising: first and second electrodes for attachment to the leg to apply an electrical stimulus; a foot switch for sensing foot rise or foot strike, said foot switch comprising a force-sensitive resistor; a circuit responsive to said foot switch for generating stimulation pulses; and means forming part of said circuit for responding to changes in the resistance characteristics of said foot switch by adjusting a corresponding response threshold of said circuit.

Various proposals have been made for providing a wireless link between a FES stimulation module and a footswitch. For example, U.S. Pat. No. 7,632,239 (Dar) discloses foot sensor device for gait enhancement comprising a sensor unit having an external casing, said sensor unit being positioned within a shoe of a user and sensing a parameter associated with a gait event An electronic communication unit is electrically associated with said sensor unit, for receiving a signal pertaining to said parameter The electronic unit has (i) a microcontroller, (ii) a transmitting module for transmitting, in a wireless fashion, gait information based on said signal, to a unit of the orthosis external to the foot sensor device, and (iii) a housing for housing at least one of said microcontroller and said transmitting unit. A fastening unit is attached to said housing, said fastening module being adapted to fasten on to said shoe, so as to secure said electronic communication module in a substantially fixed position during gait of said user and including a clamp module for fastening onto a rim of the shoe. In the field of analysing weight shift to different parts of the foot during golf or other sports U.S. Pat. No. 7,758,523 (Collings) discloses an orthotic body including an arch support, a cavity being formed in that support and a wireless transmitter being built into the cavity.

SUMMARY OF THE INVENTION

A problem with which some embodiments of the invention is concerned is how to fit a wireless footswitch including its battery into footwear unobtrusively while avoiding damage and early failure of components and providing adequate working lifetime in a single battery which in some patients is expected last at least three weeks between replacements. A further problem in embodiments of such devices is to provide low latency (e.g. about 20 milliseconds) on sending gait data e.g heel rise and heel strike from quiescent stand-by states.

In one aspect the invention provides a shoe insole having a cavity opening to its lower face and a force or pressure sensor, sensor state monitoring circuits, a wireless transceiver for transmitting sensor state information and a battery for providing power, all located in said cavity.

In another aspect the invention provides a shoe insole having a cavity configured to provide an internal pocket open to a face of said insole. The shape of the cavity may be arbitrary (e.g. it might in some embodiments be square or oval) but in preferred embodiments it has having a length greater than its width, a depth which is a small fraction of its width and is directed generally along the length of the insole, a segmented structure being slideably insertable into said cavity within it is removably retained, the segments being disposed along the cavity and housing a load or pressure sensor, sensor state monitoring circuits, a wireless transceiver and a battery, adjacent segments being electrically connected together and mechanically connected together by links configured to maintain the spacing between segments while permitting flexion between adjacent segments under loads encountered during walking.

In a third aspect the invention provides an electrical stimulator for attachment to the body comprising first and second electrodes for attachment to the body to apply an electrical stimulus, an insole as set out above, and a transceiver forming part of the simulator for communicating with the insole and providing the electrical stimulus in response to information received from the insole.

In a fourth aspect the invention provides a wireless footswitch module for fitting into a cavity formed along an insole of a shoe, said footswitch comprising a segmented structure having a length greater than its width and a depth which is a small fraction of its width, the segments housing a pressure sensor, sensor state monitoring circuits, a wireless transmitter and a battery, adjacent segments being electrically connected together and mechanically connected together by links configured to maintain the spacing between segments while permitting flexion between adjacent segments under loads encountered during walking. The elongated profile of the wireless footswitch and its segmented construction enable the wireless footswitch module to fit within the outline of the insole with its edges well within the edges of the insole and allows the device to flex longitudinally and e.g. to twist slightly to conform to the shoe profile and to accommodate walking. Advantageously the segment containing the wireless transceiver and other electrical components is located in the middle of the e.g. three segments to minimize loading.

In a fifth aspect the invention provides a footwear insole having a cavity and a load, force or pressure sensor, sensor state monitoring circuits, a wireless transceiver for transmitting sensor state information and configured to join an ad hoc wireless network (e.g. a ZigBee network), an accelerometer and a battery for providing power, all located in said cavity, the monitoring circuits being responsive to acceleration (e.g. shaking) and/or orientation detectable via the accelerometer to change from a working mode to a network joining mode. In this way a user can initiate joining between the insole with the built-in wireless footswitch module and a stimulation module without having to access switches or other devices which may be inaccessible because they are concealed within the insole. Close proximity bonding e.g. virtual contact between the modules to be joined may be necessary before joining can take place.

In a further aspect the invention provides a wireless insole for use in association with a removable wireless module, said insole having an internal cavity configured for receiving the wireless footswitch module, said cavity extending longitudinally away from a heel region of the insole and opening at an end facing away from the heel region. In some embodiments the cavity may be an elongate cavity.

In a further aspect the invention provides the use of apparatus as aforesaid in the treatment of dropped foot.

In a further aspect the invention provides a sensor module having a wireless transceiver, a microcontroller and an accelerometer and configured to communicate with a second module via an ad-hoc wireless network and to switch from a sensing mode to a network joining mode on sensing via the accelerometer a predetermined movement or movements.

DESCRIPTION OF PREFERRED EMBODIMENTS

Embodiments of the insole may be of ¾ length or full length and may be of thickness 4-10 mm. It may be a layered structure with the layers orientating themselves to form or mould to the profile of the shoe and foot. Alternatively it may be a plastic or rubber material, e.g. a silicone elastomer, the Salford Insole providing an example of such an orthotic insole. It need not have an arch support, and can be an ordinary insole having generally planar upper and lower surfaces, the insole being only a few mm in thickness so that it can be fitted to ordinary shoes or other footwear.

Embodiments of the insole have a cavity configured to provide an internal pocket having an opening to one of its faces and most conveniently its lower face into which the pressure sensor, sensor state monitoring circuits, wireless transceiver and battery are slideably insertable and within which pocket they are removably retained. The cavity in some embodiments has a length greater than its width and is directed generally along the longitudinal direction of the insole, and a combined footswitch and transceiver of segmented structure is disposed in said cavity with its segments extending along the cavity and housing or holding the sensor, sensor state monitoring circuits, wireless transceiver and battery, adjacent segments being electrically connected together and mechanically connected together as aforesaid. Embodiments of the present insole have a cavity with an aspect ratio of about 2:1 to about 4:1 e.g. about 3:1. The aspect ratio is a measure of overall length to greatest width, excluding minor components e.g. a handle for a battery carrier. The cavity is closed sat its end facing towards the heel region of the insole and opens at its end facing away from the heel, as shown in the accompanying drawings.

In embodiments the combined sensor and transceiver comprises first, second and third segments disposed in a linear chain, the second segment positioned to underlie the arch of the foot holds the sensor state monitoring circuits and transceiver, a first segment is positioned to underlie the heel (more commonly) or ball of the foot and holds the sensor and third segment holds the battery the third segment lying closest to the opening of the pocket and being provided with a handle (not counted when considering aspect ratio) by which the segmented structure can be inserted into and removed from the cavity. The handle may form part of a cell carrier that is slideably insertable endwise into and removable from the third segment.

In embodiments leads of the sensor extend from the first segment into the second segment and are held in contact with conductive regions on a circuit board forming part of said second segment by an elastomeric member in compression, e.g. a block of silicone elastomer. This arrangement permits fast replacement of the sensor without the need to make soldered connections to the circuit board in the segment which contains the active components. The battery may be a coin cell e.g. of diameter about 25 mm.

The segments in embodiments comprise plastics material e.g polyethylene, ethylene-propylene copolymer or polypropylene connected by strap connectors behaving at least to some extent as living hinges. The adjacent segments may be connected by integrally molded connectors each serving as a living hinge. In embodiments the connection is by a pair of laterally spaced connector bars, each connector bar providing links configured to maintaining the spacing between segments while permitting flexion and rotation between the adjacent segments under loads encountered during walking.

The sensor state monitoring circuits in embodiments include a microcontroller having an ADC input configured to monitor the state of the sensor, the microcontroller having a power-saving mode in which a microprocessor or core forming part of said microcontroller can be disabled while inputs continue to be active. The wireless transceiver has a stored identity for recognition by a stimulation module to which it has been joined and forming a component of a a self-organizing ad-hoc digital network e.g. obeying a Zig-Bee protocol.

The network joining mode may involve close proximity of the wireless footswitch module and the stimulation module. A predetermined movement for entry into the joining mode may comprise shaking or placing the module in a predetermined orientation. A timer forming part of the module may in some embodiments provide the joining mode to be operative for a predetermined period, after which the module reverts to standard operation.

The stimulation module may be configured for attachment to the human body or for attachment to or fitting to clothing.

BRIEF DESCRIPTION OF THE DRAWINGS

How the invention may be put into effect will now be described, by way of example only, with reference to the accompanying drawings, in which.

DETAILED DESCRIPTION OF PREFERRED EMBODIMENT

Functional Electrical Stimulation

Figure 1:
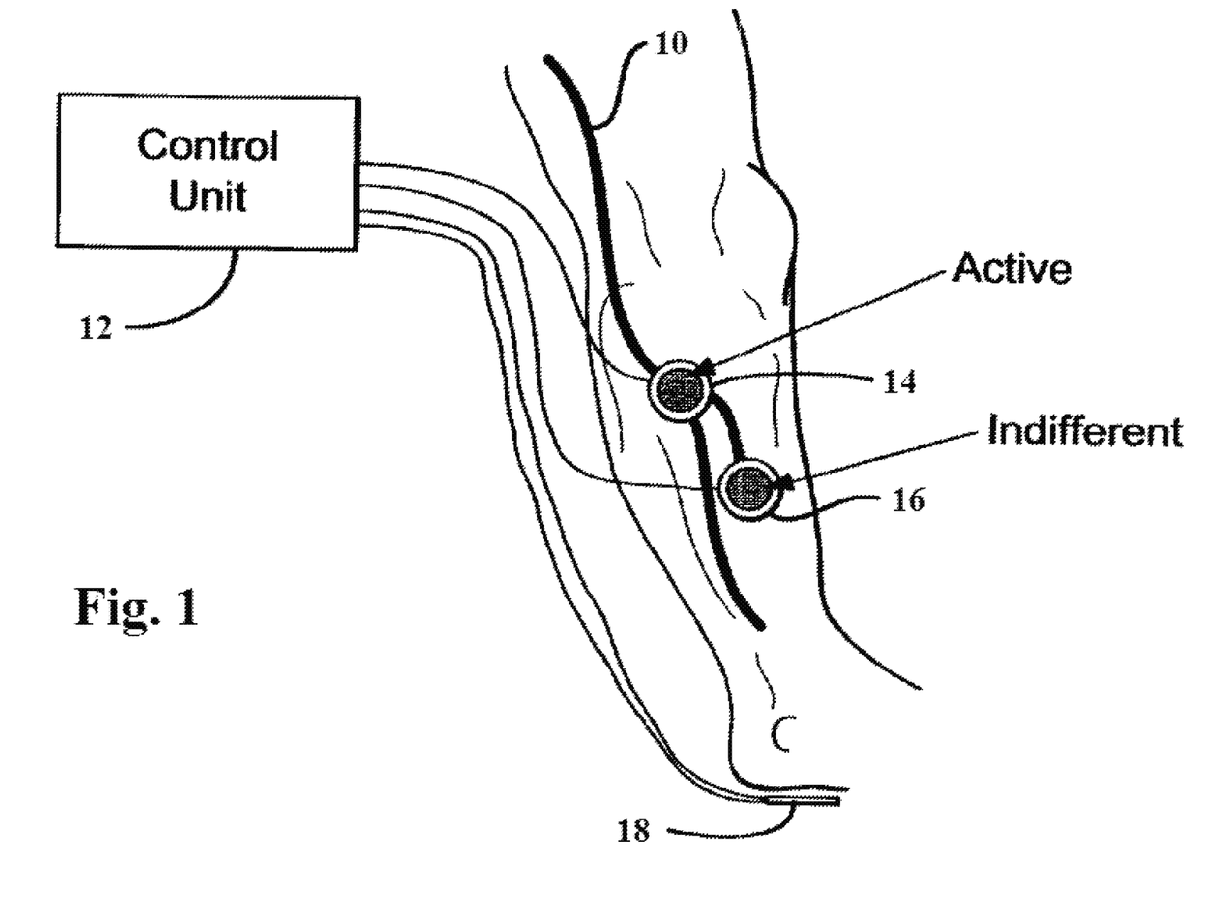
FIG. 1 shows diagrammatically a known stimulation module according to the invention with electrodes applied to the leg and a foot switch under the user's heel.

The present invention provides an improvement on known apparatus disclosed in FIG. 1 which is an electronic device designed to assist people who have a dropped foot due to neurological damage that inhibits walking. As previously explained, a dropped foot, the inability to lift a foot whilst walking, resulting in the foot being dragged forward or swung out to the side, is a common disability following neurological injury. By stimulating the common peroneal nerve at its most superficial point, passing over the head of the fibula bone, it is possible through excitation of the withdrawal reflex to cause dorsiflexion with degrees of hip and knee flexion. If this is timed with walking using a foot switch worn in the shoe, walking can be significantly improved. The stimulus gives rise to a sensation like "pins and needles" and the patient soon becomes used to it. The apparatus can be made of size e.g. 72×62×26 mm and of weight 112g including e.g. a PP3 internal battery. It can therefore be small and light enough to be worn in the pocket or on a belt clip. Wires worn under the clothing carry the electrical stimulus to self-adhesive skin surface electrodes on the side of the leg. A small foot switch is placed in the shoe under the heel. The apparatus can be used as an assistive aid or as a training device to strengthen the muscles and achieve voluntary control. Additionally the device has a role in physiotherapy gait re-education, allowing isolated components of the gait cycle to be practiced under the supervision of a therapist. Dorsiflexion and eversion in the swing phase of walking produces reduced tripping and falls, reduced compensatory activity, reduced effort of walking and improved walking speed and a reduction in patient anxiety and depression. The module is not restricted to the treatment of dropped foot, however, and it may be useful in the treatment of     gluteal or quadriceps muscles in walking     gluteal or quadriceps muscles for training weight transfer or sit-to-stand     hamstrings for increased knee flexion or reduced knee hyperextension     calf muscles for push-off at terminal stance     triceps and posterior deltoid for improved arm swing/reduced associated reaction in gait.

One way in which the known apparatus can be applied to the user's leg is shown diagrammatically in FIG. 1. The peroneal nerve 10 passes just under the head of the fibula and bifurcates to form deep and superficial branches. An active electrode 14 may be placed over the common peroneal nerve just below the head of the fibula, and an indifferent electrode 16 is located about 5 cm below and slightly medially of the active electrode over the motor point of the anterior tibialis. This is a standard position to produce a flexion withdrawal response.

The positions of the active and indifferent electrodes 14, 16 may be reversed to change the polarity of the stimulation, and in this arrangement in some cases eversion can be decreased while still producing dorsiflexion. The more negative electrode is more effective in producing stimulation than the more positive electrode so that changing electrode polarity controls the site of stimulation. Provision may be made to dynamically vary the polarity across a stream of stimulation pulses such that dorsiflexion and foot inversion/eversion can be controlled during each part of the gait cycle. Such reversal of polarity can permit muscle pairs to be controlled using a single pair of electrodes e.g. to stimulate the deep and superficial branches of the peroneal nerve. The deep branch of the peroneal nerve stimulates a group of muscles including the anterior tibialis which can produce dorsiflexion of the ankle. The superficial branch of the peroneal nerve controls the fibularis longus muscle (also known as peroneus longus) which when injured gives rise to inability to evert the foot and the fibularis brevis (peroneus brevis) muscles and thereby control foot inversion/eversion. The ability to control two groups of muscles by a single pair of electrodes is advantageous from the standpoint of patient compliance because patients find multiple electrodes in the same region of the body tedious to apply. Foot switch 18 and the electrodes 14, 16 are connected to a control module or unit 10 that includes controls and circuitry described below.

Output current in an embodiment may be adjustable between 10 and 100 mA, default 10 mA with a typical pulse width of 180 μS. The user may increase contraction strength by increasing the pulse width, compensating for day to day variations in muscle fatigue, electrode position and battery condition or changes in muscle tone.

Block Diagram of the Stimulation Module

Figure 2:
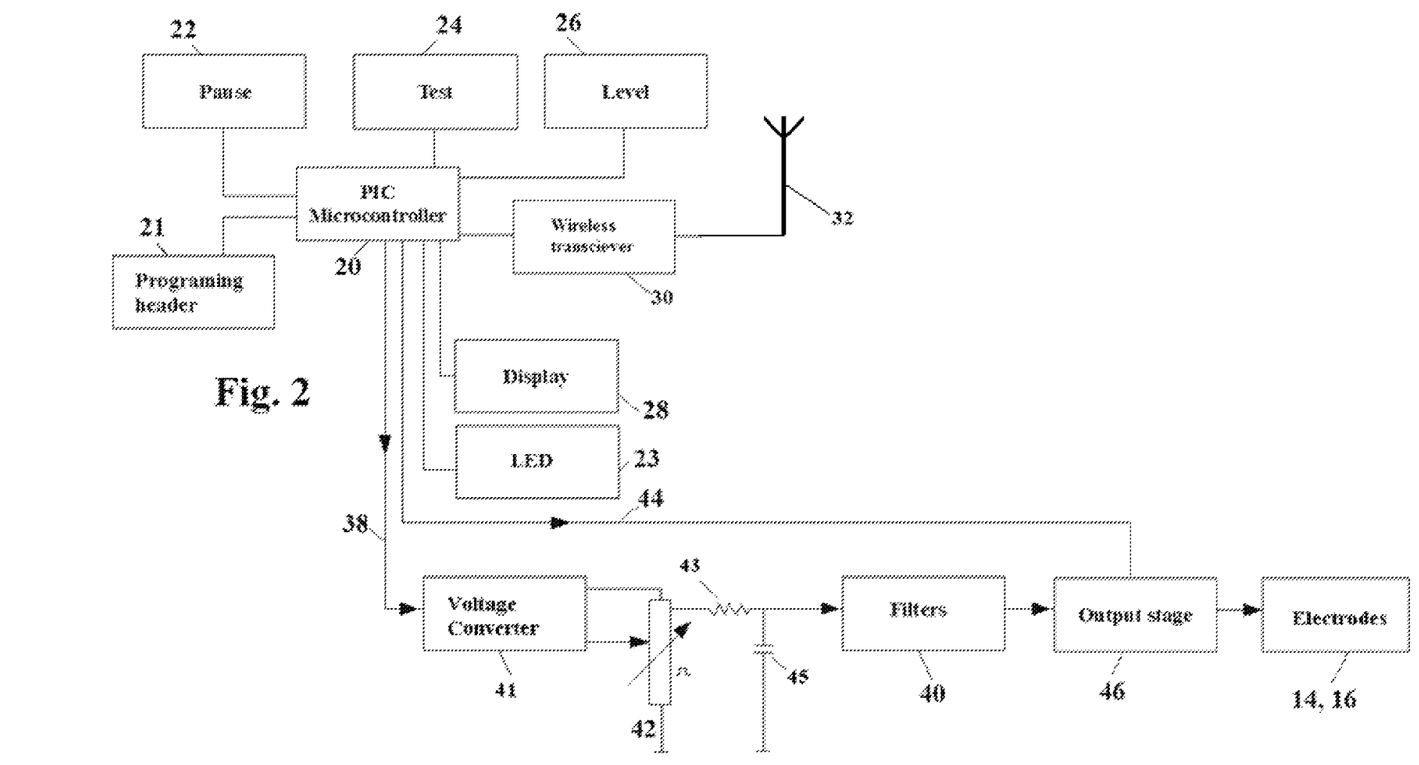
FIG. 2 is a simplified block diagram of a stimulator module forming part of a functional electrical stimulator according to the invention.

A circuit for the stimulation module 12 is shown in simplified block diagram form in FIG. 2. The module is managed by a PIC microcontroller 20 which has a stored program input by a programming header 21 and aspects of which can be adjusted by a therapist for an individual patient. An 8-bit microcontroller suffices and may in an embodiment be a microcontroller of the PIC18F4685 family available from Microchip Technology Inc. The programming header 21 permits in system programming of firmware including, as previously explained, parameters later set by the therapist using the user interface of the device.

For communication with the footswitch module the microcontroller 20 communicates with transceiver 30 provided with on-board antenna 32. The transceiver works at 2.4 GHz, complies with IEEE 802.15.4s and acts as a node of a self-organizing ad-hoc digital network, in this case complying with ZigBee. An advantage of that specification is an ability to become active from sleep mode in time of ≤20 milliseconds so that the network can be in sleep mode for much of the time, average power consumption can be kept low and battery life can be maximized.

Signals from the microcontroller 20 pass through voltage converter 41, digital potentiometer 42, a network comprising current limiting resistor 43 and capacitor 45, filters 40 and output stage 46 to electrodes 14, 16. The output stage may also be controlled by the microcontroller via lines 44. In one embodiment the output stage comprises a push-pull converter having an output transformer whose primary is controlled by a pair of 2N7002 and IRF7317 FETs and whose secondary is connected across the electrode socket. In another embodiment an output transformer has a primary connected into an H-bridge of four FETs and a secondary for connection to the electrodes. Current may pass through a first pair of transistors on supply of signals to gate inputs, or may flow through a second pair of transistor on application of signals to gate inputs. The transistors may be pulse width modulated to achieve a desired waveform and may be operated in a region where they exhibit analog-type gate voltage-response behavior. Modulating pulses are applied to their gates at frequencies which in some embodiments are in the range 200 KHz-10 MHz e.g. 2 or 8 MHz. At these frequencies the internal capacities of the transistors which are of the order of a few picofarads smooth the output waveform.

The stimulation module 12 has a number of sockets and controls for the user. A combined stimulation level and on/off switch 26 enables the contraction strength to be controlled by adjusting the stimulation pulse width from 10 to 400 μs. The switch 26 in an embodiment takes the form of a control knob which can be depressed and held down to turn the stimulation module on and can be rotated clockwise or counterclockwise to increase or decrease the output level.

An output test button 24 enables electrode positions to be tested by the therapist and by the user and can be used by the therapist when the stimulator is being used during exercising to practice components of gait. When testing the condition of the footswitch is not monitored and so the loading on the switch has no influence on the test. An output indicator LED 23 flickers when the module has been triggered. A pause switch 22 is provided that when the module is in walk or exercise mode may be used to start and stop operation of the module when pressed puts the apparatus into sleep mode, which will conserve the battery when the user sits down. To return the module to its active state, the user need only press the pause switch 22 again. A bleep is heard, and then the apparatus again responds to the foot switch. The module can only be turned off when its output has been paused, otherwise there is a risk of it being turned off accidentally while in use. To turn the stimulation module off the switch is rotated to its minimum position and the button 22 is held down. An advantage of this feature is that when the module is turned off, the pulse width setting is reduced e.g. to 1%. The user must reset the level to resume use of the module. It has been found in practice that users turn the device up through the day as their muscles become tired and having to reset the stimulation level when the device is newly turned on means that they do not receive an unexpectedly high level of stimulation when they turn the device on the next day. The recommendation for patients is that the module should therefore not be turned off using the control knob through the day but put into sleep mode using the pause switch. When the module has been turned on and is paused, a setup routine forming part of the program stored in microcontroller 20 can be accessed. This may be e.g. by depressing and holding down the switch 26 and within a predetermined period operating both the pause switch 22 and the test button 24. Details of the setup routine are disclosed in WO 2011/042736 the contents of which are incorporated herein by reference. In addition controls may be provided e.g. a sequence of operations for putting the module into joining mode where it receives a stored ID of a footswitch with which it is to communicate and a working mode, close physical proximity optionally being required to enable joining to take place.

Block Diagram of the Footswitch Module

Figure 3:
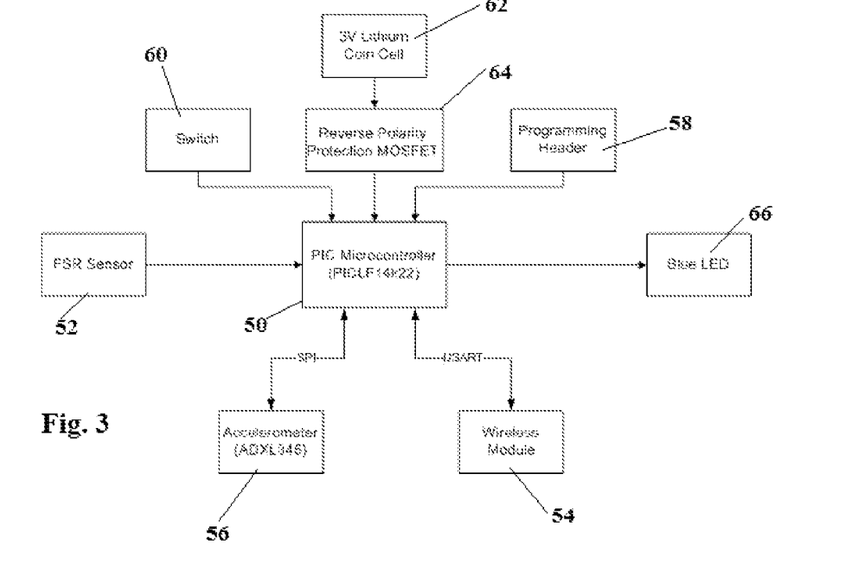
FIG. 3 is a simplified block diagram of a footswitch module for use with the stimulator module of FIG. 2.

A footswitch module or unit is shown in FIG. 3 and is based on a microcontroller 50, in this case a PIC LF14K22 which is an 8-bit microcontroller available from Microchip Technology Inc. and has a stored program input via program header 58.

The microcontroller receives signals indicating phase of walking e.g. heel rise and heel strike from a pressure sensor 52 via an ADC input and is in serial communication with wireless transceiver 54 corresponding to the transceiver 30 of the stimulation module, having an on-board antenna and complying with the ZigBee protocol. The pressure sensor is preferably a force-sensitive resistor forming part of a voltage divider as disclosed in U.S. Pat. No. 6,507,757 or WO 2011/042736 (Lane), the disclosure of which is incorporated herein by reference.

Figure 8:
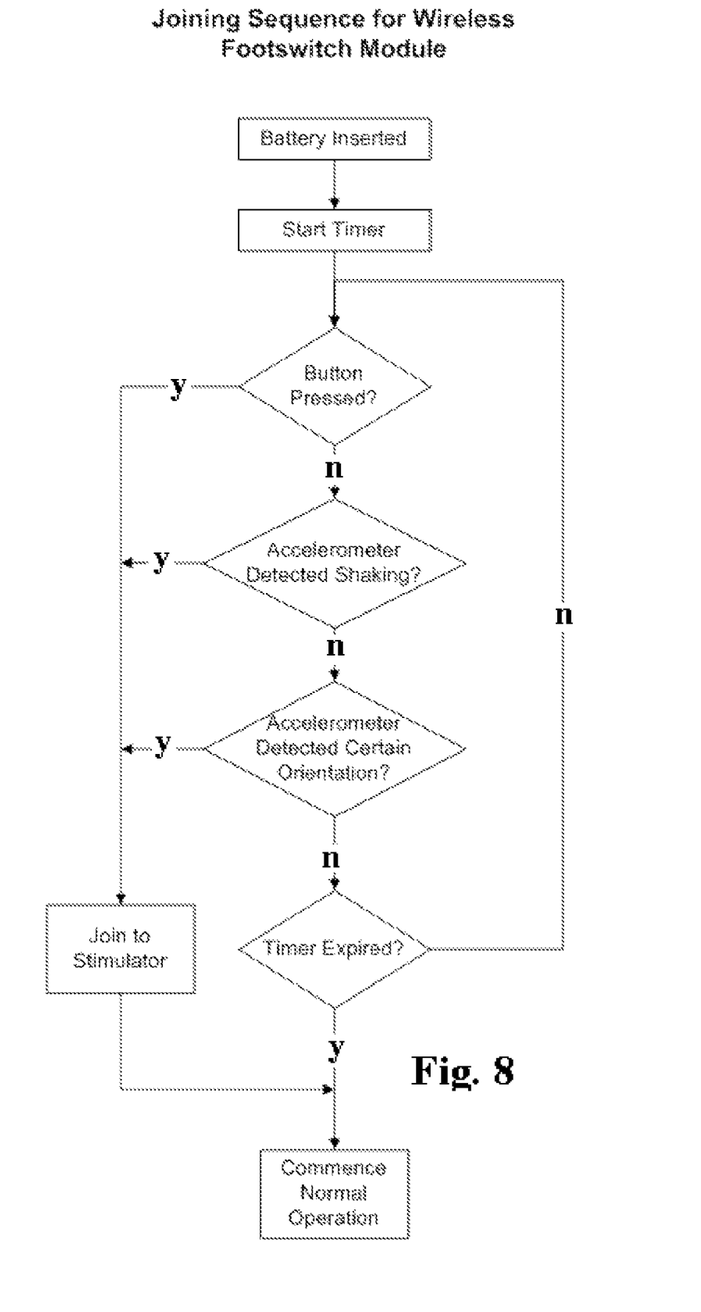
FIG. 8 is a flowchart showing how the footswitch module can be made to toggle between network joining mode and its normal sensing mode.
Figure 9:
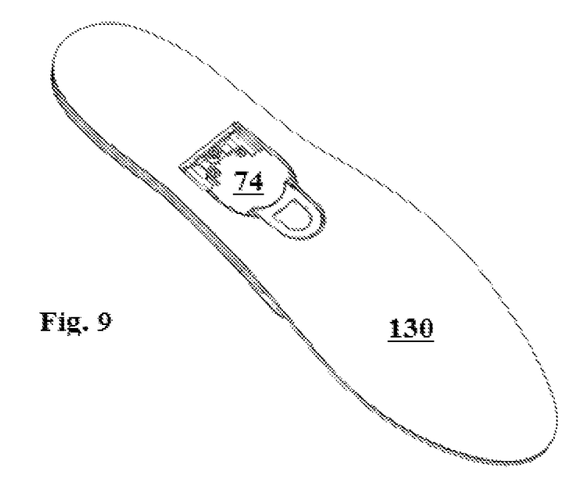
FIG. 9 is a view of a full-length insole with a segmented footswitch module as aforesaid in place in a pocket.

The microcontroller 50 is in serial communication with accelerometer 56 which may be an ADXL 345 3-axis accelerometer which has FIFO technology to minimize host processor load, provides activity/inactivity monitoring, low power or standby modes to enable intelligent motion-based power management and provides output data accessible through an SPI digital interface. It serves two functions. It can be used as a mode switch providing a "shake to join" feature e.g. on shaking of the module by the user to switch the microcontroller 50 from a working mode to a bonding mode in which the stimulation module and footswitch module share stored addresses and selective communication between them through ZigBee is enabled. The shake function has the advantage that the user can change mode of operation without having to remove the electronic module from the insole. Desirably each footswitch should only communicate with the stimulation module for which it is intended, so that if there are two people in the same room there is no cross-talk between the footswitches and stimulation modules. The accelerometer 56 can in some embodiments detect user activity/inactivity and control entry of microcontroller 50 into its working and low power states. In further embodiments it may be used to detect heel rise and heel strike during walking A flowchart for an embodiment is shown in FIG. 8, from which it will be apparent that the footswitch module enters joining mode for a predetermined time set by an internal timer which may be a stored routine (a) on pressing the switch 60 described below, (b) on the accelerometer detecting shaking or (c) on the accelerometer detecting movement of the module to a predetermined position (e.g. to an upright position). After the predetermined joining time has elapsed the module is configured to revert to its normal sensing mode e.g. its pressure-sensing mode.

As previously mentioned the footswitch module also includes a push button switch 60 which can be configured so that the module will enter joining mode for a predetermined period e.g. one minute when power is turned on and then to enter its normal working mode. The push button can be actuated through the casing via hole 93. The module also includes LED 66 for indicating the state of the circuit, e.g. the LED flashing when the module is in bonding mode. Power is supplied by 3V lithium coin cell 62 and reverse polarity protection MOSFET 64.

Segmented Footswitch Module and its Fitting to an Insole

For building a footswitch module having the components described above into a shoe insole, regard has to be had to the pressure fields acting between the plantar surface of the foot and the insole and the movement of the insole during walking Pedobarography shows that the highest pressures during walking are exerted at the heel, in the middle of the ball of the foot and at the big toe, and that pressure underneath the longitudinal arch of the foot is relatively low. Pressures will change and the sole of the user's shoe will flex during walking and it is desirable that the footswitch module should be able to withstand these forces and movements during use.

Figure 4:
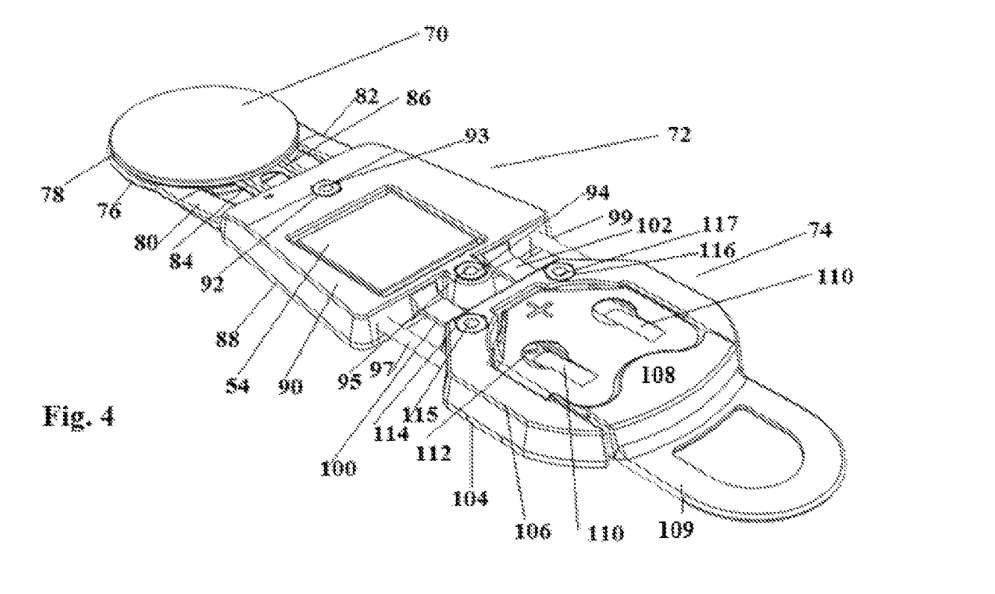
FIG. 4 is a trimetric view from above of a segmented structure removably insertable into an insole pocket and incorporating sensor, active component and battery segments mechanically connected together, some components in the block diagram not being seen in the active component segment.
Figure 5:
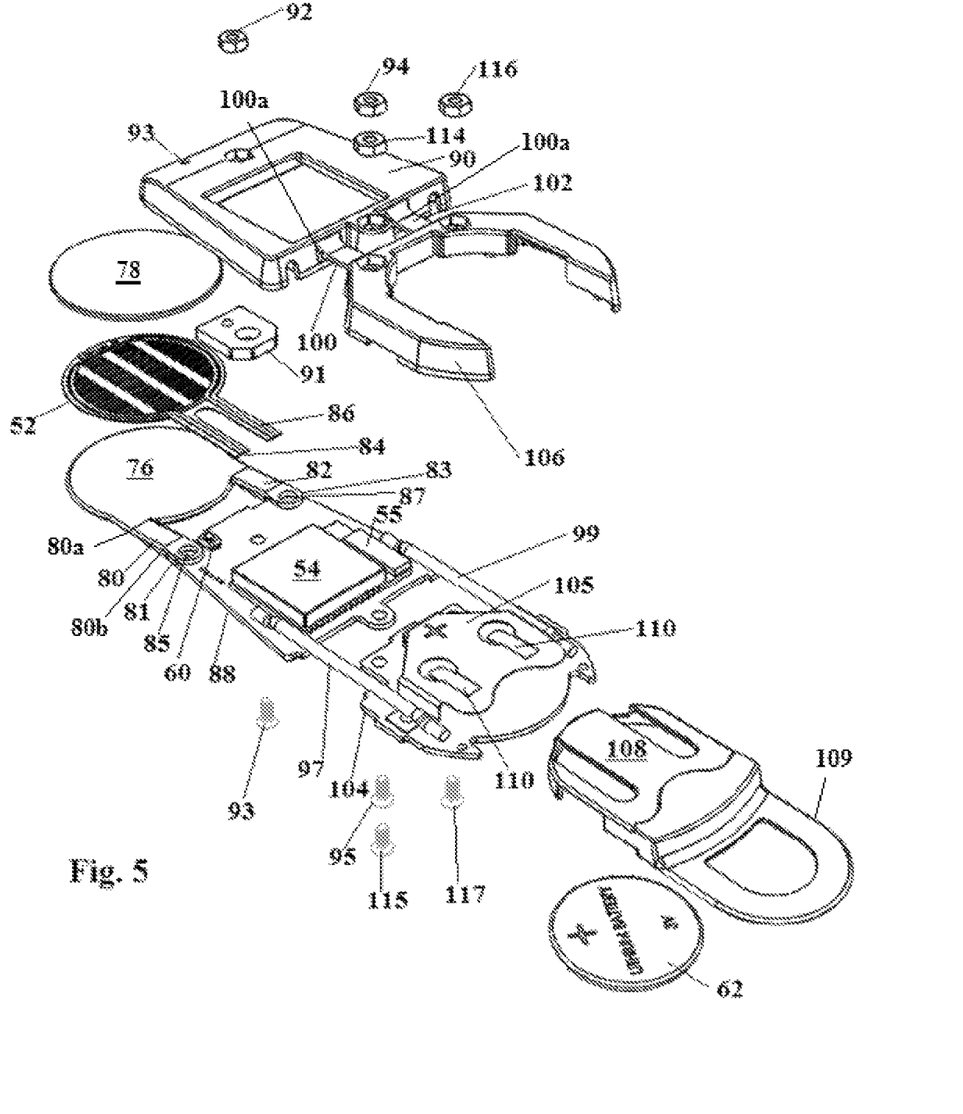
FIG. 5 is an exploded view of the segmented structure of FIG. 4.

In FIGS. 4 and 5 a segmented footswitch and transmitter structure comprises sensor segment 70, an active component segment 72 and a battery segment 74 with adjacent segments mechanically and electrically connected together, the mechanical connections maintaining the spacing between permitting the segments while permitting limited relative movement between them under the forces encountered during walking. When inserted into the insole pocket the sensor segment 70 (which most commonly underlies the user's heel) is deepest into the pocket and the battery segment 74 is closest to the opening of the pocket, the segments 72 and 74 locating between the heel and ball of the foot where they are not subject to the highest pressures during walking.

Sensor segment 70 comprises lower sheet 76 of polypropylene or other plastics material having a generally circular body and lateral connector straps 80, 82 extending towards the active component segment 72 into which they locate by passing through end slots in cover 90 with thickened end regions 81, 83 having fixing holes 85, 87 locating onto depending posts (not shown) on the concealed face of the cover 90. Each strap is stiff enough to maintain the segment spacing while permitting limited relative movement between segments e.g. at or between positions 80a, 80b. Pressure-sensor 52 is constructed as described in FIGS. 13a-13e of U.S. Pat. No. 6,507,757 (Swain) the disclosure of which is incorporated herein by reference and has a circular body of diameter about 25 mm and leads 84, 86 projecting towards and into the segment 72. A circular cover 78 of poron sheet fits onto and is adhered to lower sheet 76 with the footswitch 52 sandwiched between them and the leads 84, 86 protruding.

In embodiments the pressure sensor is of width or diameter about 25 mm and has an open-circuit resistance of ≥100 KΩ with no load applied, falling below about 5 KΩ under load. In embodiments the pressure sensor comprises a pressure-sensitive resistor having an active portion comprising an array of fingers in contact with a conductive pad so that mechanical pressure urging the pad towards the fingers reduces the resistance of the sensor. Such a pressure-sensitive resistor may comprise a first insulating plastics sheet formed with a head region and relatively narrow lead-defining extensions, conductive metal in a pattern on the plastics sheet defining an inter-digitated array connected to leads extending along said lead-defining extensions, a second insulating plastics sheet having a head conforming to the head region of the first insulating plastics sheet, and having stub projections for covering proximal regions of the lead-defining extensions of the first plastics sheet, a layer of semiconductive material on the second insulating plastics sheet, the second insulating plastics sheet having a surface with a texture or roughness or content of conductive material such that when pressed against the electrodes of the array it forms an connection between the fingers of the opposed sides of the array, and an adhesive layer securing the first and second plastics sheets together.

Active component segment 72 has a lower board 88 which is a PCB carrying the microprocessor 50 (not shown in FIG. 5), transceiver 54, on-board antenna 55, switch 60, reverse polarity protection 64 (not shown in FIG. 5), LED 66 (not shown in FIG. 5) and accelerometer 56 (also not shown in FIG. 5). Power leads 97, 99 from the battery segment 94 connect to the PCB 88. Cover 90 is fixed to the lower sheet, concealing the PCB and the components thereon save for transceiver 54 which appears through a rectangular cut-out in the cover 90 in order to minimize the depth required for segment 72. Fixing of the cover 90 over the PCB is by counter-sunk screws 93, 95 and nuts 92, 95 fitting into hexagonal recesses in the cover 90. It will be appreciated that other fastening arrangements are possible e.g. formations on the PCB 88 could snap engage with corresponding formations of cover 90.

Battery segment 74 is of polypropylene has upper and lower sheets 104, 105 and walls on three sides defining a battery receptacle with spring contacts 110 visible in this view for making electrical contact with coin cell 62 which in this instance is of diameter 24.5 mm. Leads 97, 99 extend from the battery receptacle to the active component segment 72. Battery carrier 108 is a sliding fit into the battery receptacle and has handle 109 which firstly enables battery insertion and removal and secondly facilitates placement and removal of the segmented wireless footswitch module into and from the pocket in the insole. Generally C-shaped cover 106 fits around the battery receptacle covering the leads 97, 99 at their ends extending into the segment 94 and is held in place by fixing screws 115, 117 and by nuts 14, 115 which fit into hexagonal recesses in the top face of cover 106. Again, other fitting mechanisms e.g. a snap fit arrangement are possible. The covers 90, 106 are a single injection molding in polypropylene or other flexible engineering plastics and are connected by a pair of laterally spaced straps 100, 102. Again the straps mechanically interconnect segments 72, 74 to maintain spacing between them while permitting limited relative movement under the forces encountered during walking. The aspect ratio of the segmented wireless footswitch module (not including handle 109) is about 3.

Figure 6:
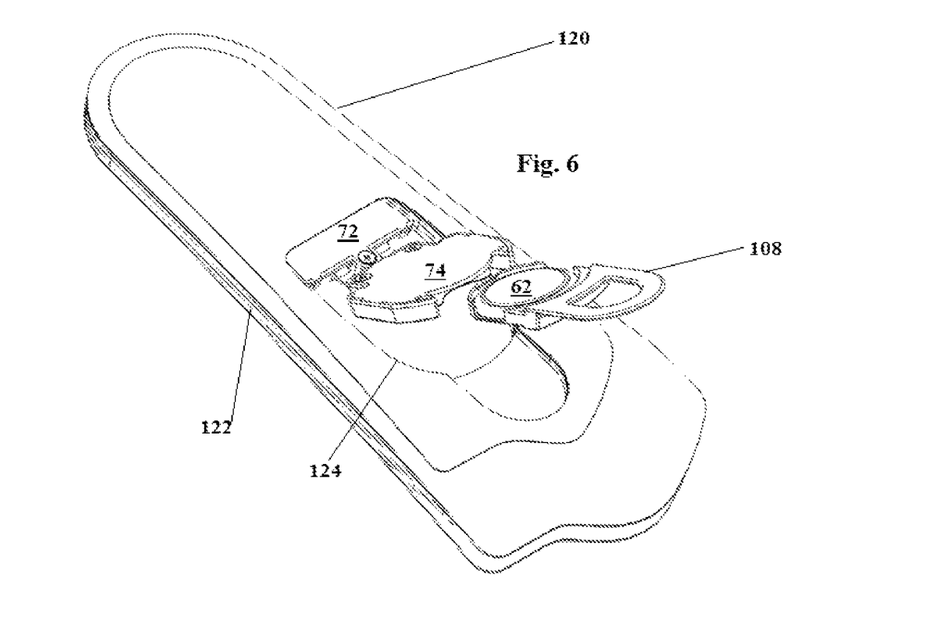
FIG. 6 is a trimetric underneath view of a ¾ insole with a segmented structure partly removed from its pocket and with a battery and carrier removed from the battery segment.
Figure 7:
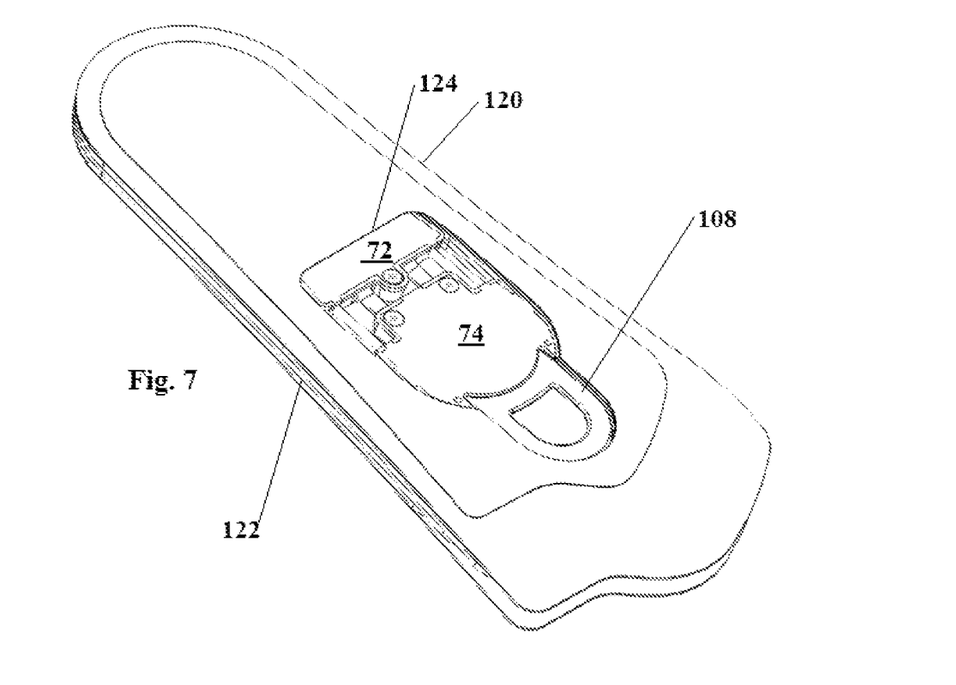
FIG. 7 is a trimetric underneath view of the insole of FIG. 6 with the segmented structure in place in the pocket.

FIGS. 6 and 7 show the segmented wireless footswitch module fitted to a pocket in the underside of ¾ length insole 120 of depth 4-5 mm which is formed in layers 122, pocket 124 opening to the lower face of the insole and the upper face (not shown) being plain so that the module is wholly concealed within the insole. Pillars (not shown) within the layers limit relative sliding movement of the layers and may assist in prolonging the useful life of the insole. The insole material may be mixed and not necessarily produced from material of a single composition or physical properties. The layers may be soft or hard (different densities) as required to produce an insole that flexes to accommodate walking but also enables effective actuation of the sensor segment 70. FIG. 8 is an underneath view of a full length insole which for some users may reduce in-shoe insole movement, a segmented footswitch module fitting into a pocket as before in insole 130.

It will be appreciated that modifications may be made to the embodiment described above without departing from the invention. For example if it were desired to monitor both heel strike and toe-off an additional footswitch could be fitted to the module described above. Provision may be made so that an OML footswitch can be attached to the middle PCB 88 and trigger the wireless module as would the sensor 52. This requirement may arise (a) if the clinician desires to trigger from the first metatarsal head and not the heel and (b) for those which the insole cannot fit in their footwear and the wireless footswitch module is worn outside of the shoe. Although the ZigBee protocol is preferred, other networking protocols could be used or the two transceivers could simply be made in matched pairs as is conventional in low power radio applications. If monitoring of both feet is required, then an insole with a wireless footswitch module could be provided for each foot, and both could be proximity bonded to the same stimulation module.

The invention claimed is:

1. A shoe insole for use in functional electrotherapy having a cavity opening to its lower face and a wireless footswitch module located in said cavity, wherein said footswitch module comprises:
    a load, force or pressure sensor;
    a microcontroller for receiving signals from the sensor indicating phase of walking and having a power-saving mode in which a microprocessor or core forming part of said microcontroller can be disabled while inputs continue to be active;
    a wireless transceiver in communication with the microcontroller for transmitting sensor state information;
    a battery for providing power; and
    an accelerometer for monitoring user activity/inactivity and controlling entry of the microcontroller into working and power-saving modes; wherein the accelerometer is a 3-axis accelerometer having FIFO technology for minimising host processor load, has low power or standby modes for intelligent motion-based power management and has an SPI digital interface for providing output data.

2. The shoe insole of claim 1, wherein the wireless transceiver is configured to operate according to a ZigBee protocol.

3. The shoe insole of claim 1, wherein the cavity is configured to provide a pocket within said insole having an opening to the lower face of the insole into which the wireless footswitch module is slideably insertable and within which pocket it is retained until removed.

4. The shoe insole of claim 3, wherein the cavity has a length greater than its width and is directed generally along the longitudinal direction of the insole, and wherein the module is a segmented structure is disposed in said cavity with its segments extending along the cavity and holding the sensor, sensor state monitoring circuits, wireless transceiver and battery, adjacent segments being electrically connected together and mechanically connected together by links configured to maintain the spacing between segments while permitting flexion between adjacent segments under loads encountered during walking.

5. The shoe insole of claim 4, wherein one of said segments is positioned to underlie the arch of the foot and holds the sensor state monitoring circuits and transmitter, a second segment which holds the sensor is positioned to underlie the heel of the foot or to underlie the ball of the foot and a third segment holds the battery which is a coin cell.

6. The shoe insole of claim 5, wherein the sensor is a pressure-sensitive resistor an open-circuit resistance of ≥100 KΩ with no load applied, falling below about 5 KΩ under load, the sensor having an active portion comprising an array of fingers in contact with a conductive pad so that mechanical pressure urging the pad towards the fingers reduces the resistance of the sensor.

7. The shoe insole of claim 6, wherein the sensor comprises:
    a first insulating plastics sheet formed with a head region and relatively narrow lead-defining extensions;
    conductive metal in a pattern on the plastics sheet defining an inter-digitated array connected to leads extending along said lead-defining extensions;
    a second insulating plastics sheet having a head conforming to the head region of the first insulating plastics sheet, and having stub projections for covering proximal regions of the lead-defining extensions of the first plastics sheet;
    a layer of semiconductive material on the second insulating plastics sheet, the second insulating plastics sheet having a surface with a texture or roughness or content of conductive material such that when pressed against the electrodes of the array it forms an connection between the fingers of the opposed sides of the array; and
    an adhesive layer securing the first and second plastics sheets together.

8. The shoe insole of claim 7, wherein leads of the sensor extend from the sensor segment into the active component segment and are held in contact with a circuit board forming part of said active component segment by an elastomeric member in compression.

9. The shoe insole of claim 8, wherein the elastomeric member comprises a block of silicone elastomer.

10. The shoe insole of claim 1, further comprising:
    first and second electrodes for attachment to a body to apply an electrical stimulus; and
    a transceiver communicating with the microcontroller and providing the electrical stimulus via the first and second electrodes in response to information received from the transceiver.

11. An electrical stimulator for attachment to a body, comprising:
- first and second electrodes for attachment to the body to apply an electrical stimulus;
- a shoe insole for use in functional electrotherapy having a cavity opening to its lower face and a wireless footswitch module located in said cavity, wherein said footswitch module comprises a load, force or pressure sensor, a microcontroller for receiving signals from the sensor indicating phase of walking and having a power-saving mode in which a microprocessor or core forming part of said microcontroller can be disabled while inputs continue to be active, a wireless transceiver in communication with the microcontroller for transmitting sensor state information, a battery for providing power and an accelerometer for monitoring user activity/inactivity and controlling entry of the microcontroller into working and power-saving modes; and
- a transceiver forming part of the simulator for communicating with the insole and providing the electrical stimulus via the first and second electrodes in response to information received from the insole; wherein the accelerometer is a 3-axis accelerometer having FIFO technology for minimizing host processor load, has low power or standby modes for intelligent motion-based power management and has an SPI digital interface for providing output data.

12. The electrical stimulator of claim 11, wherein:
the cavity is configured to provide a pocket within said insole having an opening to the lower face of the insole into which the wireless footswitch module is slideably insertable and within which pocket it is retained until removed.

13. The electrical stimulator of claim 12, wherein:
the cavity has a length greater than its width and is directed generally along the longitudinal direction of the insole, and wherein the module is a segmented structure is disposed in said cavity with its segments extending along the cavity and holding the sensor, sensor state monitoring circuits, wireless transceiver and battery, adjacent segments being electrically connected together and mechanically connected together by links configured to maintain the spacing between segments while permitting flexion between adjacent segments under loads encountered during walking; and
one of said segments is positioned to underlie the arch of the foot and holds the sensor state monitoring circuits and transmitter, a second segment which holds the sensor is positioned to underlie the heel of the foot or to underlie the ball of the foot and a third segment holds the battery which is a coin cell.

14. The electrical stimulator of claim 11, wherein the sensor is a pressure-sensitive resistor an open-circuit resistance of ≥100 KΩ with no load applied, falling below about 5 KΩ under load, the sensor having an active portion comprising an array of fingers in contact with a conductive pad so that mechanical pressure urging the pad towards the fingers reduces the resistance of the sensor.

15. The electrical stimulator of claim 11, wherein the sensor comprises:
- a first insulating plastics sheet formed with a head region and relatively narrow lead-defining extensions;
- conductive metal in a pattern on the plastics sheet defining an inter-digitated array connected to leads extending along said lead-defining extensions;
- a second insulating plastics sheet having a head conforming to the head region of the first insulating plastics sheet, and having stub projections for covering proximal regions of the lead-defining extensions of the first plastics sheet;
- a layer of semiconductive material on the second insulating plastics sheet, the second insulating plastics sheet having a surface with a texture or roughness or content of conductive material such that when pressed against the electrodes of the array it forms an connection between the fingers of the opposed sides of the array; and
- an adhesive layer securing the first and second plastics sheets together, wherein leads of the sensor extend from the sensor segment into the active component segment and are held in contact with a circuit board forming part of said active component segment by a block of silicone elastomer or other elastomeric member in compression.

16. A wireless footswitch for use in functional electrotherapy comprising in combination:
- a removable shoe insole comprising a single cavity configured to provide an internal pocket open to a face of said insole at an opening, the cavity having a length greater than its width and being directed generally along the length of the insole; and
- a single segmented structure having a length greater than its width and configured for slidable insertion through said opening in said face of said sole endwise into said cavity, said structure being inserted into said cavity within which it is removably retained;
- the segments being disposed along the cavity and housing a pressure sensor, sensor state monitoring circuits, a wireless transmitter and a coin cell battery;
- adjacent segments being electrically connected together and being mechanically connected together by flexible hinge links configured to maintain the spacing between segments while permitting flexion between adjacent segments under loads encountered during walking; and
- the single segmented structure having first, second and third segments disposed in a linear chain wherein a first segment houses the pressure sensor, a second segment located in a middle of said first, second and third segments houses the sensor state monitoring circuits and wireless transmitter and a third segment holds the coin cell battery.

17. The wireless footswitch of claim 16, wherein the sensor is a pressure-sensitive resistor having an array of fingers in contact with a conductive pad so that mechanical pressure urging the pad towards the fingers reduces the resistance of the sensor and comprising:
- a first insulating plastics sheet formed with a head region and relatively narrow lead-defining extensions;
- conductive metal in a pattern on the plastics sheet defining an inter-digitated array connected to leads extending along said lead-defining extensions;
- a second insulating plastics sheet having a head conforming to the head region of the first insulating plastics sheet, and having stub projections for covering proximal regions of the lead-defining extensions of the first plastics sheet;
- a layer of semiconductive material on the second insulating plastics sheet, the second insulating plastics sheet having a surface with a texture or roughness or content of conductive material such that when pressed against the electrodes of the array it forms an connection between the fingers of the opposed sides of the array; and an adhesive layer securing the first and second plastics sheets together, leads of the sensor extending from the sensor segment into the active component segment and being held in contact with a circuit board forming part of said active component segment by a block of silicone elastomer or other elastomeric member in compression.

18. A wireless footswitch for use in functional electrotherapy comprising in combination:

a removable shoe insole comprising a single cavity configured to provide an internal pocket open to a face of said insole at an opening, the cavity having a length greater than its width and being directed generally along the length of the insole; and a single segmented structure having a length greater than its width and configured for slideable insertion through said opening in said face of said sole endwise into said cavity;

the segments being disposed along the cavity and housing a pressure sensor, sensor state monitoring circuits, a wireless transmitter, and a coin cell battery;

adjacent segments being electrically connected together and being mechanically connected together by links configured to maintain the spacing between segments while permitting flexion between adjacent segments under loads encountered during walking, said links being either strap connectors behaving as living hinges or a pair of laterally spaced connector bars, each connector bar providing links maintaining the spacing between segments while permitting flexion and rotation between the adjacent segments under loads encountered during waking; and the segmented structure having first, second and third segments disposed in a linear chain wherein a first segment houses the pressure sensor, a second segment located in a middle of said first, second and third segments houses the sensor state monitoring circuits and wireless transmitter and a third segment holds the coin cell battery.

\* \* \* \* \*